(12) United States Patent
Girshovich et al.

(10) Patent No.: US 6,894,512 B2
(45) Date of Patent: May 17, 2005

(54) METHOD FOR DETECTING HIDDEN CORROSION AND A SENSOR FOR USE IN THE SAME

(75) Inventors: Simon Girshovich, Kfar Saba (IL); Mordechai Gelchinski, Ramat Gan (IL); William Reginiano, Ramat Gan (IL)

(73) Assignee: Israel Aircraft Industries Ltd., Lod (IL)

(*) Notice: Subject to any disclaimer, the term of this patent is extended or adjusted under 35 U.S.C. 154(b) by 0 days.

(21) Appl. No.: 10/395,862

(22) Filed: Mar. 24, 2003

(65) Prior Publication Data

US 2004/0189331 A1 Sep. 30, 2004

(51) Int. Cl.[7] .............................................. G01R 27/08
(52) U.S. Cl. ........................................ 324/694; 338/35
(58) Field of Search ........................... 324/694; 338/34, 338/35

(56) References Cited

U.S. PATENT DOCUMENTS

| | | | |
|---|---|---|---|
| 4,673,910 A | * 6/1987 | Uchikawa et al. | ............. 338/35 |
| 4,877,646 A | 10/1989 | Kuhn | |
| 4,942,364 A | * 7/1990 | Nishijima et al. | .......... 324/694 |
| 4,975,317 A | 12/1990 | Kuhn | |
| 5,108,829 A | 4/1992 | Kuhn | |
| 5,304,295 A | 4/1994 | Kim | |
| 5,338,432 A | * 8/1994 | Agarwala et al. | ............ 205/118 |
| 5,446,369 A | 8/1995 | Byrne | |
| 5,549,803 A | 8/1996 | Schoess | |
| 5,674,752 A | * 10/1997 | Buckley et al. | ................ 338/34 |
| 6,629,934 B2 | * 10/2003 | Mault et al. | ................. 600/538 |
| 2001/0054965 A1 | 12/2001 | Blum | |

FOREIGN PATENT DOCUMENTS

| | | |
|---|---|---|
| EP | 0 329 436 | 8/1989 |
| EP | 0 349 105 | 1/1990 |
| EP | 0 783 050 | 7/1997 |
| WO | WO 01/81897 | 1/2001 |

OTHER PUBLICATIONS

V.T. Truong, A Sensor For Water Detection in Aircraft Adhesive Bondlines, Maritime Platforms Division . . . DSTO–RR–0172, May 2000, Melbourne, Australia

* cited by examiner

Primary Examiner—Anjan Deb
Assistant Examiner—Timothy J. Dole
(74) Attorney, Agent, or Firm—Lilling & Lilling P.C.

(57) ABSTRACT

The present invention provides a method for determining whether or not moisture appeared in a hidden place during a period T, the method comprising: (i) introducing to the hidden place a moisture sensitive element; the moisture sensitive element comprising: a) a dielectric substrate coated or impregnated with an intrinsically conducting polymer and b) probes connecting the substrate to a resistance meter; (ii) measuring and recording the electrical resistance of the substrate at two or more times during the period T; (iii) determining whether or not moisture appeared in the hidden place during the period T according to the changes in the electrical resistance of the moisture sensitive element that occurred during period T. The present invention further provides method and system for alerting against a possible appearance of corrosion in a hidden place, a moisture sensor for use in the method or system, and a method for producing a substrate comprised in such a moisture sensor.

19 Claims, 3 Drawing Sheets

METHOD FOR DETECTING HIDDEN CORROSION AND A SENSOR FOR USE IN THE SAME

FIELD OF THE INVENTION

This invention relates to a method for detecting hidden corrosion and a sensor for use in the same.

LIST OF REFERENCES

The following is a list of references that are considered to be relevant as background to the invention. Appearance of a document in this list should not be construed as implying that the document is relevant to the patentability of the invention.

Truong et al., DSTO Aeronautical and Maritime Research Laboratory, Australia, May (2000);

U.S. Pat. No. 4,877,646;
U.S. Pat. No. 4,975,317;
U.S. Pat. No. 5,108,829;
U.S. Pat. No. 5,446,369; and
U.S. Pat. No. 5,549,803.

BACKGROUND OF THE INVENTION

Hidden and inaccessible corrosion of metal structures is an unavoidable problem, in spite of all contemporary technological protection means, since almost all environments are corrosive to a certain degree. In particular, moisture in the air along with its atmospheric content (acids, salts and organic compounds) can penetrate within almost any metallic structure and cause corrosion.

When corrosion occurs on outward surfaces, it may be observed by visual checking. More difficult is the detection of corrosion inside structures, when it is hidden between different structure elements. In order to verify the existence of hidden corrosion inside of such structures it is necessary to disassemble the entire structure, an action that is very expensive and sometime practically impossible.

The problem of early detection of hidden corrosion is crucial in maintenance of aging aircraft Conventional non-destructive inspection (NDI) techniques such as X-ray radiography, eddy current, ultrasonic, acoustic emission, etc. are used to solve this problem but are not always reliable in detecting hidden and inaccessible corrosion.

U.S. Pat. No. 5,549,803 describes a smart fastener laving corrosion detection features for detecting hidden corrosion in aircraft structures. Within the fastener there is a corrosion array which receives an electrolyte that corrodes sacrificial materials formed on the electrodes of the corrosion detecting-array. The information sensed by the corrosion sensing electrodes of the array is in the form of very small electrical signals that are amplified and stored in an analog storage memory. An interface circuit enables a user to electronically access corrosion and related signals without removing or in any way dismantling the fastener.

U.S. Pat. No. 5,446,369 describes a corrosion monitor system to facilitate the detection and monitoring of material corrosion in remote areas. Sensors, which react to a corrosive environment similar to the material to be monitored, are placed in isolated areas and connected to a central control system via shielded cables. The system operates on the principle that corrosion of a metallic conductor will cause a corresponding increase in the cross-sectional electrical resistance of that conductor. This change in resistance can be detected and monitored by passing a known constant current through the conductor and comparing the voltage across the conductor with that of a controlled reference conductor which is not exposed to the corrosive environment.

Truong et al. developed a sensor for water detection in aircraft adhesive bond lines by embedding a compressed polypyrrole powder in an epoxy adhesive sandwiched between two aluminum substrates. An interaction between polypyrrole and water resulted in a rapid increase in both DC and AC resistivity.

SUMMARY OF THE INVENTION

Detection of water or moisture inside of metallic structures, is a good predictor for the development of corrosion within these structures, therefore being an important factor in monitoring the health of an aging aircraft.

Thus, according to the first aspect thereof, die present invention provides a method for determining whether or not moisture appeared in a hidden place during a period T, the method comprising:

(i) Introducing to the hidden place a moisture sensitive element: the moisture sensitive element comprising: a) a dielectric substrate coated or impregnated with an intrinsically conducting polymer and b) probes for connecting said substrate to a resistance meter;

(ii) measuring and recording the electrical resistance of said moisture sensitive element at two or more times during the period T;

(iii) determining whether or not moisture appeared in said hidden place during the period T according to the changes in die electrical resistance of said moisture sensitive element that occured during period T.

The present invention further provides a method for alerting against a possible appearance of corrosion in a hidden place, comprising:

(i) determining whether or not moisture appeared in the hidden place during a period T, by the method described above;

(ii) if moisture is determined to appear during the period T, creating an alert that corrosion has possibly appeared in the hidden place.

According to another aspect thereof, the present invention provides a system for alerting against a possible appearance of corrosion in a hidden place, comprising:

(i) a moisture sensitive element to be placed in said the hidden place, said moisture sensitive element comprising; a) a dielectric substrate coated or impregnated with an intrinsically conducting polymer and b) probes for connecting said substrate to means for measuring the resistance thereof, (ii) means for measuring the electrical resistance of said moisture sensitive element at different times;

(iii) means for storing the electrical resistance values of said moisture sensitive element at two or more different times;

(iv) means for analyzing the title development of the electrical resistance of to said moisture sensitive elements to determine whether or not moisture appeared in said hidden place during period T;

(v) means for alerting that corrosion has possibly appeared; said means being operable upon determination that moisture appeared by the means specified in (iv).

The hidden place wherein the appearance of moisture is detected according to the preset invention may be any inaccessible place that includes corrodable substance, and the accession thereto is difficult or expensive. Non-limiting examples for such places are: an aircraft wing, wing to fuselage attachment, structure under the passenger floor, bonded structures, lavatory, galley, etc. Such hidden place may also be under a paint layer on an inner or outer skin of an object such as aircraft.

The means for determining the electrical resistance of the moisture sensitive element according to the invention are any means known in the art per se, such as ohmmeter, wheatstone bridge, resonance circuits, etc.

The means for storing the electrical resistance according to the invention may be any means known in the art per se, be it electrical, magnetic, mechanical means, or any other kind of storing means. Some non-limiting examples of such storing means are a digital memory, a magnetic tape and a plot (which serves also as a display).

The means for evaluating the change of the electrical resistance of the moisture sensitive element with time may be any means known per se, such as a microprocessor, a visual analysis of a plot plotted from the stored data, and the like.

The alerting means may be of any kind known per se, non-limiting examples of these are loudspeaker, calling when an alert is set, a light turning on, an SMS or email message being sent, and a person shouting.

The present invention further provides a moisture sensor including a moisture sensitive element comprising a dielectric substrate coated or impregnated with an intrinsically conducting polymer and probes for connecting the substrate to a resistance-meter, wherein the moisture sensitive element being located in a hidden place.

The present invention further provides an aircraft comprising such a moisture sensor.

Further to the moisture sensitive element of die present invention and uses thereof, the present invention also provides a method for producing such a moisture sensitive element. More specifically, the present invention provides a method for coating or impregnateing a dielectric textile material with an intrinsically conductive polymer; the method comprising:

i) impregnating the dielectric textile material in a first solution containing a monomer of an intrinsically conductive polymer;

ii) inserting the impregnated dielectric textile material obtained in i) into a second solution containing a suitable dopant and a polymerizing agent;

iii) waiting a predetermined period of time until the polymerization reaction is completed;

iv) drying the coated textile material in air, at room temperature, so as to obtain a dry textile material coated with an intrinsically conductive polymer.

The term "predetermined period of time" mentioned in step iii) above is a value that is calculated according to several preceding tests, carried out in similar conditions, as the time for obtaining a single coating of a polymer.

In order to obtain coated fabrics having larger conductivity values, the procedure mentioned above may be repeated for several times until the conductivity obtained is satisfactory.

According to a preferred embodiment of the invention, the second solution mentioned in step ii) above further comprising a complexing agent.

Non-limiting examples of suitable dopants for use in the method of the present invention are anthraquinone-2-sulfonic acid, naphthalene-2-sulfonic acid, 5-sulfosalicylic acid and toluensulfonic acid.

The polymerizing agent used in the method of the invention is a chemical oxidant that nay be a compound of polyvalent metal ion or a compound not containing a polyvalent metal ion. Non-limiting examples of suitable polymerizing agents for use in the method of the present invention are $FeCl_3$, $Fe_2(SO_4)_3$, $K_3Fe(CN)_6$, $H_3PO_4 \cdot 12MoO_3$, $H_3PO_4 \cdot 12WO_3$, $CrO_3$, $(NH_4)_2Ce(NO_3)_6$, $CuCl_2$ $AgNO_3$, nitriles, quinones, peroxides, peracids, persulfates, perborates, permanganates, perchlorates and chromates.

Non-limiting examples of suitable complexing agent for use in the invention are, aromatic, hydroxycarboxylic acids, and aromatic, hydroxysulfonic acids.

BRIEF DESCRIPTION OF THE DRAWINGS

In order to understand the invention and to see how it may be carried out in practice, specific embodiments will now be described, by way of non-limiting examples only, with reference to the accompanying drawings, in which.

DETAILED DESCRIPTION OF THE INVENTION

Figure 1A:
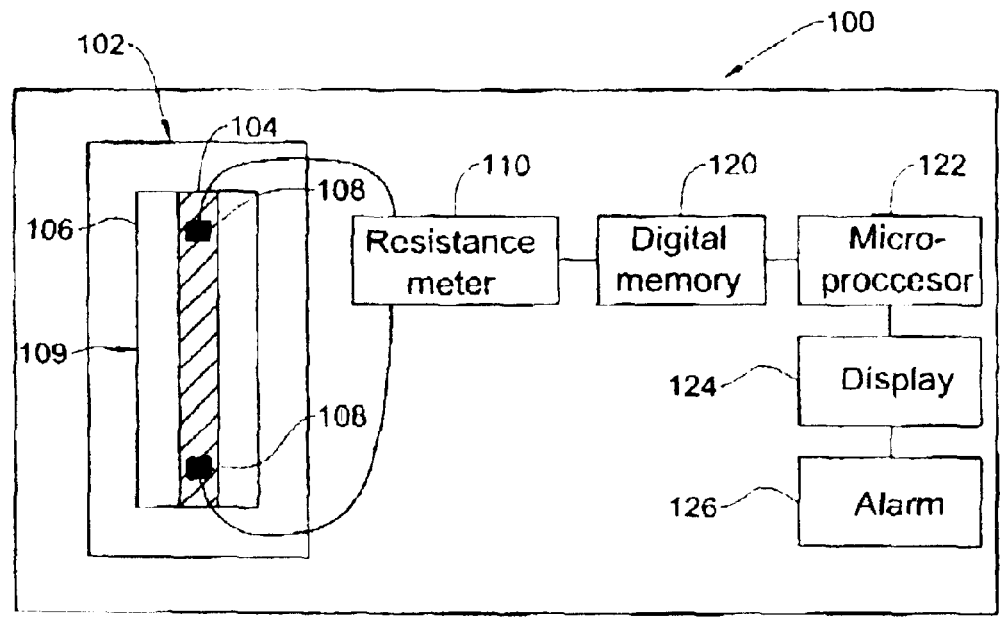
FIGS. 1A and 1B are schematic illustrations of two systems according to the present invention.

FIG. 1A illustrates system 100 according to the present invention. The system 100 comprises an non-accessible enclosure 102, which is a hidden place, with a moisture sensitive element 104 introduced therein. The moisture sensitive element 104 includes: a dielectric fabric coated with an intrinsically conducting polymer 186 and probes 108 for connecting the moisture sensitive element 104 to a resistance meter 110. In addition, the moisture sensitive element 104 further comprises a frame 109 for holding the dielectric fabric 106, in this embodiment the resistance meter 110 is located in an accessible place, apart of the moisture sensitive element, 104. The resistance meter 110 is connected to a digital memory 120, which is connected to a microprocessor 122. The microprocessor 122 is connected to a display 124 and to an alarm loudspeaker 126.

Figure 1B:
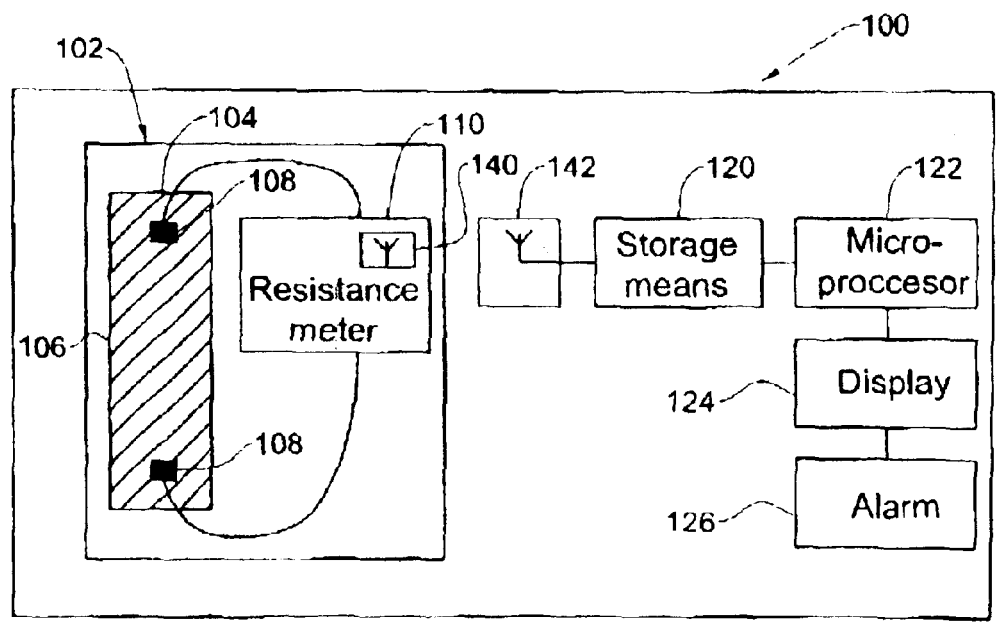

FIG. 1B illustrates a similar system, where numeral references equal to those used in FIG. 1A are used to refer to the same elements. In FIG. 1B the resistance meter 110 is enclosed in the hidden place 102 and transmits its readings through an antenna 140 to another antenna 142, connected to the storage means 120.

In operation, the electrical resistance of the moisture sensitive element 104 is measured by the resistance meter 110 at cast at the beginning and at the end of a period T to obtain records $R_1$ and $R_2$, respectively, and possibly also records of the resistance in different times during the period T. The various resistance values that were recorded during the period T are analyzed by the microprocessor 122 to determine whether moisture appeared in the hidden place 102 or not. If moisture is determined to appear, the alarm 126 is turned on. The display 124 shows a graph of the resistance measured versus the time lapsed from the beginning of the period T, such that a qualified person (not shown) that observes the graph may find an indication for the appearance of moisture even in case the alarm 126 is out of order.

The resistance meter 110, the storage means 120 and the processor 122 may be located apart from each other, and information, for instance, from the storage means 120 to the processor 122, may be transmitted either along transmission wires or, preferably, by wireless transmission means. One such a transmission means suitable for use according to the invention is Bluetooth.

The algorithm, according to which the microprocessor 122 determines whether moisture appeared in the enclosure 102 during period T or not, compares the time development of the electrical resistance of the element 104 to that of a similar element, given in a moisture-free environment for a similar period. Alternatively, the comparison may be against a similar element given in a moisture-containing environment, and preferably both kinds of comparison are used.

Any statistical characteristic, such as average, median, variance, etc., may be used to characterize the time development of the electrical resistance of the measuring element and of the control element in order to facilitate the comparison between them, and possibly also to obtain a statistical evaluation of the probability that a given set of results was obtained despite the absence of moisture, and to produce an alert when this probability is smaller than a predetermined value.

Typically, the time development of the resistance of a moisture sensitive element according to the invention is more rapid in the presence of moisture than in the absence thereof. Furthermore, resistance values do not decrease when moisture disappears, and therefore, averages of long periods may be used to determine appearance or non-appearance of moisture without the concern that a transient appearance of moisture will go undetected.

According to one embodiment of the invention, in order to determine that moisture has appeared in a hidden place during a period T, $R_2$ should be significantly higher than $R_1$. The meaning of the term significantly higher may be determined by conducting well controlled experiments, in which the differences in the resistance of a moisture sensitive element during different periods of time and wider various conditions of humidity and temperature are measured, and analyzing the obtained results by the appropriate statistical tests, as well known in the art.

As well known in the art, electrical resistance of an element is directly related to its electrical conductivity, therefore, all resistance measurements needed according to the invention may be replaced by conductivity measurements. Furthermore, all conductivity/resistance measurements may be conducted either under DC or under AC conditions. Conductivity or resistance measuring means are well known in the art, and include, for example, ohmmeters, Wheatstone bridges, resonance circuits, etc.

Dielectric substance suitable for use according to the invention may be a glass, a rubber, a plastic, a conducting material coated with a primer or a fabric. Preferably the fabric is a knitted, woven or non-woven fabric. Preferable fabrics include fibers selected from polyester, polyamide, acrylic, polybenzimidazole, glass and ceramic.

The intrinsically conductive polymer suitable for use according to the invention may be any such polymer that irreversibly changes its electrical conductivity upon exposure to moisture. According to the specific use of the moisture sensitive element, the conductive polymer included therein should have suitable thermal stability (typically, thermal stability is needed for up to at least 70° C.), mechanical strength and elasticity. Some non-limiting examples of intrinsically conductive polymers suitable for use in the present invention are polyaniline, polythiophene, polypyrrole, mixtures and copolymers thereof The moisture sensitive element according to the invention may be attached to the inner walls of the hidden place where it should sense the appearance of moisture, for instance, to the inner wall of an aircraft wing. In order to prevent differences in electrical potential between the inner walls and the moisture sensitive element, it may be advisable to coat the inner walls with a primer or other suitable paint that includes an intrinsically conducting polymer.

The term) "probes" used herein encompasses any element suitable for connecting the moisture sensitive element to the resistance meter. However, in some embodiments the probes are connecting the moisture sensitive element located inside the hidden place to a resistance-meter located in an accessible place. In such a case care should be taken to construct the probes strong and reliable enough to ensure constant contact between the probes and the moisture sensitive element under every possible condition.

The present invention further provides a moisture sensor including a moisture sensitive element comprising a dielectric fabric coated with an intrinsically conducting polymer and probes for connecting the moisture sensitive element to a resistance-meter, wherein the moisture sensitive element being located in hidden place.

According to one embodiment of the invention, the sensor further comprises a resistance meter which may be located in a hidden place and is further connected to means for storing and transferring the results measured by the resistance meter to an accessible display. According to another embodiment, the resistance meter is itself in an accessible place, and only the moisture sensitive element is located in the hidden place.

Non-limiting examples of means for storing and transferring the results measured by the resistance meter are a transmitter and a memory unit.

The moisture sensor of the present invention may further comprise a frame for holding the dielectric coated substrate. The frame is preferably made of a conducting material and is usually used to support the coated substrate.

The present invention provides according to another aspect thereof, an aircraft comprising a moisture sensor according to the invention.

According to a preferred embodiment thereof the present invention provides such an aircraft wherein the moisture sensor further comprises a resistance meter. Preferably, the moisture sensitive element is located in a hidden place and more preferably, the resistance measured by the resistance meter is being displayed in an accessible place.

The textile material used in fabricating the moisture sensor according to the invention may be a fabric, filament, fiber or yarn. A fabric suitable for use in the method of the invention may be a knitted, woven or nonwoven fabric and it preferably comprises fibers selected from polyester, polyamide, acrylic, polybenzimidazole, glass and ceramic.

A coated fabric suitable for use in the sensor of the present invention may be prepared by methods known in the art. For instance, by the method described in U.S. Pat. No. 4,877,646. This patent described a method for making electrically conductive textile materials under agitation conditions with an aqueous solution of a pyrrole compound, an oxidizing agent and a doping agent or counter ion and then depositing onto the surface of individual fibers of the fabric a prepolymer of the pyrrole compound. In case wherein the oxidizing agent is a ferric salt, the aqueous solution further contains a weak complexing agent for ferric ions to effectively control the polymerization reaction rate.

U.S. Pat. No. 4,975,317 describes a method for imparting electrical conductivity to textile materials by contacting the textile material with an aqueous solution of an oxidatively polymerizable compound selected from pyrrole and aniline and an oxidizing agent capable of oxidizing the above compound to a polymer in the presence of a counter ion or doping agent.

U.S. Pat. No. 5,108,829 provides a textile material rendered electrically conductive by a polypyrrole film deposited on the textile material by chemical oxidation of pyrrole in an aqueous solution also containing an oxidizing agent and anthraquinone-2-sulfonic acid as a dopant.

A coated fabric suitable for use in the sensor of the present invention may be also prepared by the method of the present invention. A specific example for the preparation of a coated fabric according to the invention is described under Example 1 below.

A sensor for use in the present invention may also include, as a moisture sensitive element a substrate coated with a paint which comprises intrisically conductive polymer. The substrate may be for instance, an outer or an inner skin of an aircraft coated with an epoxy primer. The epoxy primer used is preferably according the standard MIL-PRF-23377. The layer of the paint that comprises intrinsically conductive polymer may be further coated with another layer of polyurethane.

EXAMPLES

Example 1 Preparation of a Conducting Fabric

Two solutions are prepared:
Solution A:
   pyrrole 40 ml/l
   Ethanol
solution B:
   $FeCl_3$) 40 g/l
   anthraquinone-2-sulfonic acid 4 g/l
   5-sulfosalicylic acid dihydrate 4 g/l
   distilled water Stage 1: impregnation A piece of woven polyester fabric is immersed in a solution A for a period of 1 hour. The fabric is then taken out of the solution and the excess solution is left to drip for several minutes with so squeezing to obtain a fabric absorbed with solution A.

Stage 2: Polymerization

The fabric obtained in stage 1 is inserted into a vessel containing solution B, at room temperature, for a period of about 5 hours to obtain a fabric coated with polypyrrole.

The coated fabric is washed with water to remove from its surface a black powder. The black powder is polypyrrole which is not confined to the fabric surface.

The fabric is dried in the air, at room temperature, to obtain a fabric having an electrical resistance value of between 800 to 1000 ohms per square as determined according to standard ASTM D257. The above process may be repeated several times and thus the obtained fabric will have a smaller electrical resistance. A single coat provides a fabric having a surface electrical resistance of 1000 ohms per square.

Example 2 Changes in the Resistance of a Moisture Sensitive Element as a Function of the Moisture Present in the Environment A Moisture Sensitive Element:

A moisture sensitive element is prepared by providing a coated fabric having a thickness of 0.5 mm, prepared according to the procedure described in Example 1 above, and inserting it between two aluminum plates having dimensions of 10×6×2 mm. The two aluminum plates constitute a frame for holding the coated fabric or may model two skins, between which the sensor is inserted.

Figure 2:
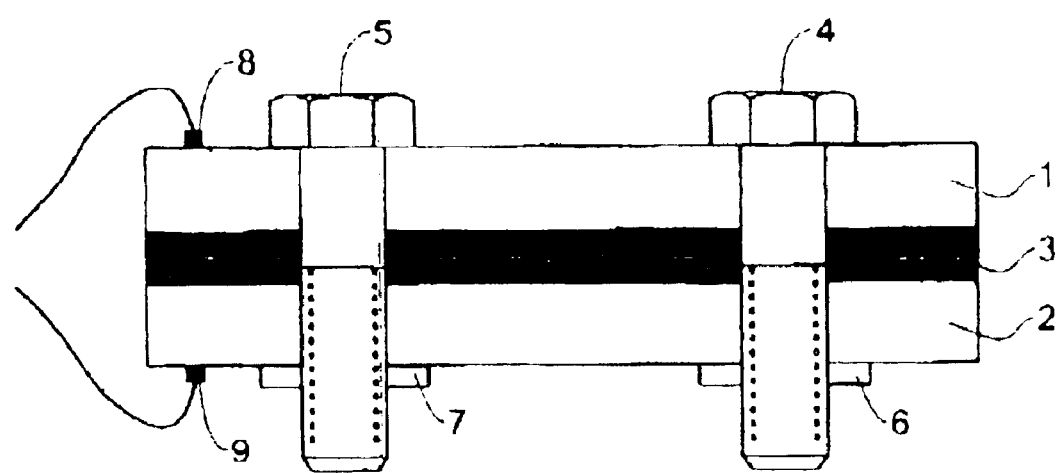
FIG. 2 is a schematic illustration of a moisture sensitive element according to one embodiment of the invention.

An illustration of such moisture sensitive element is presented in FIG. 2.

The two aluminum plates 1 and 2 are attached to each other by screws 4 and 5 and screw-nuts 6 and 7. The screw-nuts 6 and 7 are made of plastic, in order to avoid an electrical contact between the plates 1 and 2 and the screws 4 and 5.

Each plate 1 and 2, respectively, has a probe 8 and 9 for connecting the moisture sensitive element of FIG. 2 to an ohmmeter (not shown).

The fabric 3 had an initial electrical resistance of 85 Ω.

A moisture cell:

A desiccator containing the above moisture sensitive element is used for measuring the changes in the resistance of the moisture sensitive element as a function of the moisture present in the desiccator at various conditions.

When the desiccator containing silica gel, the relative humidity inside of it reaches a value of 19%, after a period of about 5 hours.

When the bottom of the desiccator is filled with water instead of silica gel, the relative humidity inside it reaches a value of 99%, after a period of about 8 hours.

Figure 3:
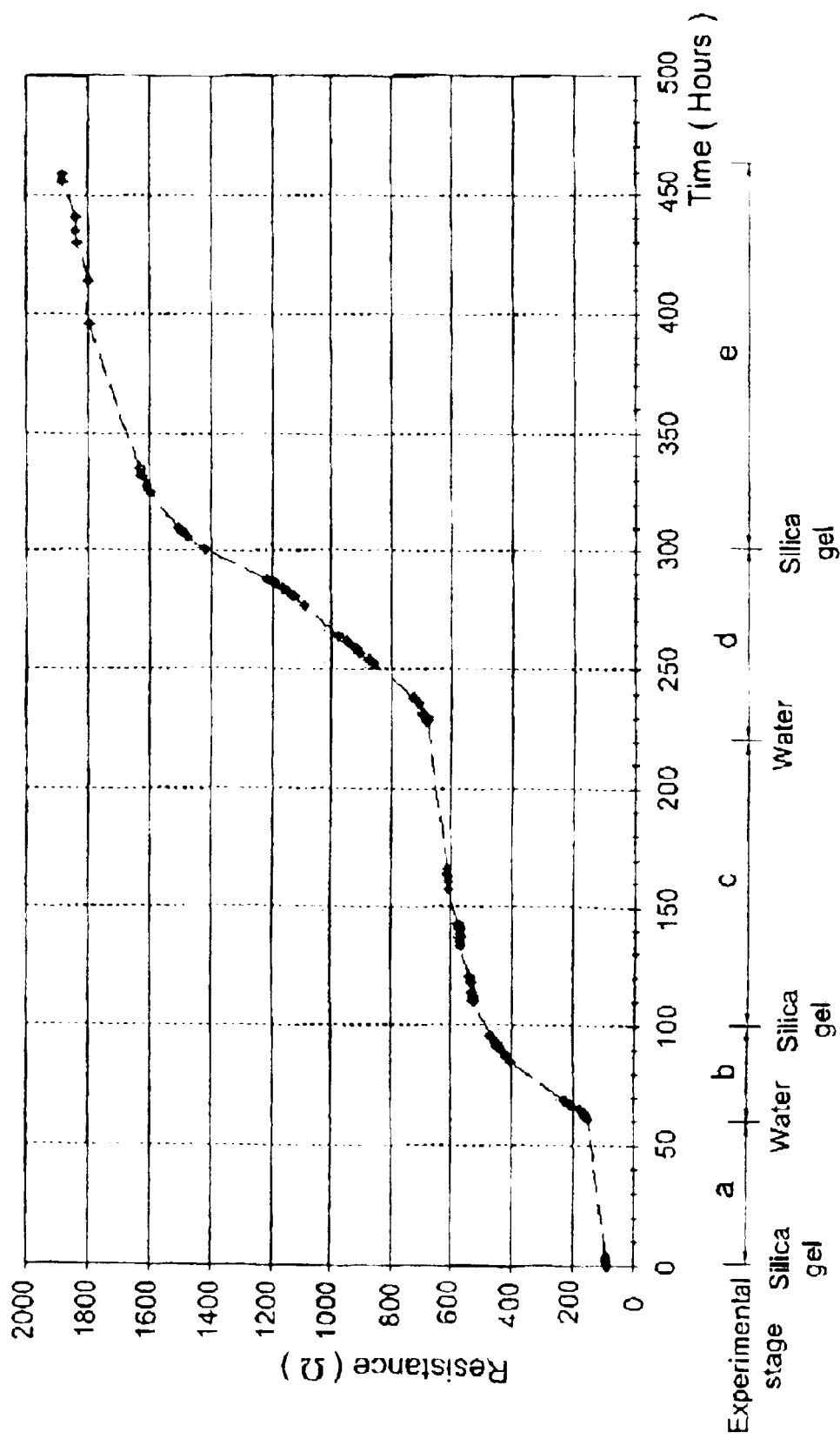
FIG. 3 is a graph showing the time development of the electrical resistance of a moisture sensitive element according to the invention, in the presence of water at some times and in the absence of water at other times, as described in detail below.

FIG. 3 describes the changes of the resistance of the moisture sensitive element as a function of time, during which samples of water and silica gel are inserted into the desiccator as described below.

Experimental Procedure:

Stage a:

The moisture sensitive element is inserted into the desiccator containing silica gel for a period of 62 hours. When the average moisture in the desiccator is 19%, a mild change in the resistance of the moisture sensitive element is observed. The resistance of the moisture sensitive element raises from 85Ω(the initial value) to 155Ω, which is a change of about 1.11% per hour.

Stage b:

The moisture sensitive element is taken out of the desiccator and instead of silica gel, about 300 ml of water are inserted into the desiccator. The moisture sensitive element is inserted again into the desiccator, in a way that there is no contact between the moisture sensitive element and the water (the moisture sensitive element is placed on a ceramic surface above the water). The desiccator is closed and an immediate rise in the resistance is observed. The moisture sensitive element is kept in this situation for a period of 38 hours and in that period of time, the resistance is changed from 155Ω to 500Ω, which is a change of about 91% per hour.

Stage c:

After that the water is taken out of the desiccator and the desiccator is dried and filled again with silica gel.

The moisture sensitive element is inserted again into the desiccator for a period of 120 hours. Staying in a relative low moisture percentage stopped the step rise in the resistance of the moisture sensitive element At this stage, the resistance is changed from 500Ω to 680Ω, which is a change of about 1.25% per hour.

Stage d:

The desiccator is filled again with water and the moisture sensitive element is inserted into the desiccator for a period of 80 hours. At this period of time, when the relative moisture reaches a value of about 99%, the resistance is changed from 680Ω to 1400Ω, which is a change of about 9% per hour.

Stage e:

The water is taken out of the desiccator and the desiccator is dried and filled again with silica gel. The moisture sensitive element is inserted again into the desiccator for a period of 150 hours. Staying in a low relative humidity stopped the steep rise in the resistance of the moisture sensitive element (see FIG. 3). At this period of time, the resistance is changed from 1400Ω to 1860Ω, which is a change of about 3% per hour.

Other functions of the time development of the electrical resistance, such as, for example, $\Delta \ln R/\Delta T$, may also be used for such an analysis.

What is claimed is:

1. A method for determining whether or not moisture appeared in a hidden place during a period T, the method comprising:
   (i) introducing to said hidden place a moisture sensitive element; said moisture sensitive element comprising: a) a dielectric substrate coated or impregnated with an intrinsically conducting polymer and b) probes connected to said substrate and to a utility for measuring electrical resistance of said substrate;
   (ii) measuring and recording said electrical resistance of said substrate at two or more times during the period T;
   (iii) determining whether or not moisture appeared in said hidden place during the period T according to the changes in the electrical resistance of said moisture sensitive element that occured during period T.

2. A method according to claim 1 wherein moisture is determined to appear if resistance measured at the end of the period T is significantly higher than resistance measured at the beginning of period T.

3. A method according to claim 1 wherein each of said probes has one end located inside said hidden place and another end located in an accessible place.

4. A method according to claim 1, wherein said intrinsically conductive polymer is selected from polyaniline, polythiophene, polypyrrole, mixtures and copolymers thereof.

5. A method according to claim 1, wherein said dielectric substrate is selected from a glass, a rubber, a plastic, a conducting material coated with a primer or a knitted, woven or non-woven fabric.

6. A method according to claim 5, wherein said knitted, woven or non-woven dielectric fabric comprises fibers selected from polyester, polyamide, acrylic, polybenzimidazole, glass and ceramic.

7. A method according to claim 5 wherein said dielectric substrate is made of a conducting material coated with a primer, and said primer is a paint comprising intrinsically conductive polymer.

8. A method according to claim 1, wherein said hidden place is located inside of an aircraft or under a paint layer.

9. A method according to claim 8, wherein said paint layer is located on an inner or outer skin of an aircraft.

10. A method according to claim 8, wherein said hidden place is located at an aircraft wing, wing to fuselage attachment, structure under the passenger floor, bonded structures, lavatory or galley.

11. A method for determining whether or not moisture appeared in a hidden place during a period T, the method comprising:
   (i) introducing to said hidden place a moisture sensitive element; said moisture sensitive element comprising: a) a dielectric substrate coated or impregnated with an intrinsically conducting polymer that irreversably changes its electrical conductivity upon exposure to moisture and b) probes connected to said substrate and to a utility for measuring electrical resistance of said substrate;
   (ii) measuring and recording said electrical resistance of said substrate at least at the beginning and at the end of the period T;
   (iii) determining whether or not moisture appeared in said hidden place during the period T according to the changes in the electrical resistance of said moisture sensitive element that occured during period T.

12. A method for determining whether or not moisture appeared in a hidden place during a period T, the method comprising:
   (a) introducing to said hidden place a moisture sensitive element; said moisture sensitive element comprising: a) a dielectric substrate coated or impregnated with an intrinsically conducting polymer and b) probes connected to said substrate and to a utility for measuring electrical resistance of said substrate, wherein said dielectric substrate is selected from a glass, a rubber, a plastic, a conducting material coated with a primer or a knitted, woven or non-woven fabric and wherein said dielectric substrate is made of a conducting material coated with a primer, and said primer is a paint comprising intrinsically conductive polymer;
   (b) measuring and recording said electrical resistance of said substrate at two or more times during the period T;
   (c) determining whether or not moisture appeared in said hidden place during the period T according to the changes in the electrical resistance of said moisture sensitive element that occurred during period T.

13. A method according to claim 12 wherein moisture is determined to appear if resistance measured at the end of the period T is significantly higher than resistance measured at the beginning of period T.

14. A method according to claim 12 wherein each of said probes has one end located inside said hidden place and another end located in an accessible place.

15. A method according to claim 12, wherein said intrinsically conductive polymer is selected from polyaniline, polythiophene, polypyrrole, mixtures and copolymers thereof.

16. A method according to claim 12, wherein said knitted, woven or non-woven dielectric fabric comprises fibers selected from polyester, polyamide, acrylic, polybenzimidazole, glass and ceramic.

17. A method according to claim 12, wherein said hidden place is located inside of an aircraft or under a paint layer.

18. A method according to claim 17, wherein said paint layer is located on an inner or outer skin of an aircraft.

19. A method according to claim 17, wherein said hidden place is located at an aircraft wing, wing to fuselage attachment, structure under the passenger floor, bonded structures, lavatory or galley.

* * * * *